(12) United States Patent
Yoneda et al.

(10) Patent No.: US 6,610,879 B2
(45) Date of Patent: Aug. 26, 2003

(54) REACTION METHOD BY USING HETEROGENEOUS CATALYST AND REACTION APPARATUS THEREFOR

(75) Inventors: Yukihiro Yoneda, Himeji (JP); Tetsuya Kajihara, Himeji (JP); Yasuhiro Shingai, Himeji (JP); Hajime Matsumoto, Himeji (JP); Tokumasa Ishida, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 76 days.

(21) Appl. No.: 09/901,011

(22) Filed: Jul. 10, 2001

(65) Prior Publication Data

US 2002/0016494 A1 Feb. 7, 2002

(30) Foreign Application Priority Data

Jul. 31, 2000 (JP) ........................................ 2000-231206

(51) Int. Cl.[7] .............................. C07C 69/52; B01J 8/00
(52) U.S. Cl. ........................ 560/205; 560/209; 560/218; 422/238; 422/239; 261/94; 261/97; 261/107; 261/122.1; 261/113
(58) Field of Search ............................ 261/94, 97, 107, 261/122.1, 113; 422/238, 239; 560/205, 209, 218

(56) References Cited

U.S. PATENT DOCUMENTS

| | | | |
|---|---|---|---|
| 2,772,780 A | 12/1956 | Penick | ........................ 210/42.5 |
| 3,253,053 A | 5/1966 | Bergougnou et al. | .. 260/683.43 |
| 3,584,685 A * | 6/1971 | Boyd et al. | |
| 3,882,167 A | 5/1975 | Lohmar et al. | ......... 260/486 R |
| 4,365,081 A * | 12/1982 | Shimizu et al. | |
| 4,833,267 A | 5/1989 | Nakashima et al. | .......... 60/205 |
| 5,892,103 A * | 4/1999 | Sogabe et al. | |

FOREIGN PATENT DOCUMENTS

| | | |
|---|---|---|
| GB | 1056496 | 8/1963 |
| WO | WO 94/16807 | 8/1994 |

* cited by examiner

*Primary Examiner*—Porfirio Nazario-Gonzalez
(74) *Attorney, Agent, or Firm*—Roylance, Abrams, Berdo & Goodman, L.L.P.

(57) ABSTRACT

When carrying out a liquid-phase reaction by using a heterogeneous catalyst, the separation of the heterogeneous catalyst and the reaction liquid is carried out certainly and effectively. A reaction method involves carrying out a reaction in liquid phase by using a heterogeneous catalyst particle 30 in a reactor 10, and comprises the steps of: (a) allowing a reaction liquid 40 supplied into the reactor 10 from such as a supplying inlet 12 to react in the presence of the heterogeneous catalyst particle 30, and (b) passing the resultant reaction liquid 40 containing the heterogeneous catalyst particle 30 through a line screen 20 having an opening width where the heterogeneous catalyst particle 30 is not allowed to pass substantially, and then extracting the reaction liquid 40 separated from the heterogeneous catalyst particle 30 from the reactor 10 by way of such as an extracting outlet 14.

10 Claims, 7 Drawing Sheets

(a)

(b)

(a)

(b)

(a)

(b)

(c)

(a)

(b)

(c)

REACTION METHOD BY USING HETEROGENEOUS CATALYST AND REACTION APPARATUS THEREFOR

BACKGROUND OF THE INVENTION

A. Technical Field

The present invention relates to a reaction method by using a heterogeneous catalyst such as an ion-exchange resin particle as a catalyst, and a reaction apparatus used in this reaction method. More particularly, the present invention aims, for example, reactions for producing (meth)acrylate by use of (meth)acrylic acid.

B. Background Art

Reaction methods which involves carrying out a reaction in liquid phase by using an ion-exchange resin as a catalyst, are known as a method (fixed bed reaction method) which involves using a reactor fix-packed with an ion-exchange resin or a method (fluidized bed reaction method) which involves canning out a reaction in a state that the ion-exchange resin is suspended and dispersed in a reaction liquid, and separating the reaction liquid and the ion-exchange resin after the reaction.

It is believed that the fluidized bed reaction method is preferable because its reaction efficiency can be improved.

JP-A-54326/1974 proposes a method which involves introducing a gas from the bottom of a reactor so that an ion-exchange resin can be suspended and dispersed in a reaction liquid, and separating the reaction liquid and the ion-exchange resin by use of a catalyst-separating apparatus comprising a filter. In addition, JP-A-17844/1988 proposes a method which involves suspending and dispersing an ion-exchange resin in a reaction liquid by use of stirrer, and separating the reaction liquid and the ion-exchange resin by use of a wire mesh of 80 mesh placed at the bottom of a vessel.

In the fluidized bed reaction method among the above conventional methods, when carrying out the separation of the ion-change resin and the reaction liquid by use of the filter or the wire mesh, the filter or the wire mesh is clogged with such a cracked ion-exchange resin during the reaction or a side-produced polymer in the reaction. Therefore, it becomes difficult to operate for a long time and the cracked ion-exchange resin becomes easily leaked.

For example, in case of the reaction to produce (meth)acrylate by allowing (meth)acrylic acid to react with alcohols, there was a problem that the hydrolysis was further caused by the ion-exchange resin as leaked. In addition, when the above reaction was continuously carried out, there was a problem that the effective resin amount was deceased with the passage of time and the reaction rate was lowered because of ununiform flow caused by such clogs. A sedimentation method is considered as effective means of separating the ion-exchange resin from the reaction mixture. However, the apparatus becomes larger according to this method. In addition, there is a defect that it takes much time to separate them.

In addition, in the conventional means of separating the ion-exchange resin and the reaction liquid in the above way, the piling portion of the ion-exchange resin and the reaction liquid is caused when carrying out the separation. Therefore, the reaction further proceeds while piling. However, in this case, the reaction becomes heterogeneous because the liquid and the resin do not flow, and impurities increase because the side reaction goes ahead.

Particularly, in case of exothermic reactions such as a reaction to produce hydroxyalkyl (meth)acrylate by allowing alkylene oxide to react with (meth)acrylic acid, it is difficult to remove heat at the piling portion. Therefore, the extraordinary rise of temperature is caused. At the portion of high temperature, the polymerization of such as (meth)acrylic acid as a raw material or hydroxyalkyl (meth)acrylate as a product is easily caused, and furthermore the problem of the above clogs is caused.

In addition, in the fixed bed reaction method, the wire mesh is easily clogged with the resin having a small diameter or a side-produced polymer. At the clogged portion, it is difficult for the liquid to flow, and the reaction liquid is piled up. The, the effective portion to carry out the reaction becomes less. Because of causing the piling portion in the reactor, not only the reactivity lowers and the side reaction increases but also the polymerization of the raw material and the product is accelerated and the operation becomes difficult.

In reactions other than the reaction by using the ion-exchange resin, the same problem is also caused in the reaction method which involves carrying out a reaction in liquid phase by using various heterogeneous catalysts.

SUMMARY OF THE INVENTION

A. Object of the Invention

An object of the present invention is that: when carrying out a separation of a heterogeneous catalyst and a reaction liquid, the separation of the heterogeneous catalyst and the reaction liquid can be carried out certainly and effectively by using a compact apparatus with inhibiting the side reaction or the polymerization and avoiding unstable operation due to clogs of the heterogeneous catalyst.

B. Disclosure of the Invention

A reaction method by using a heterogeneous catalyst, according to the present invention, is a method which involves carrying out a reaction in liquid phase by using a heterogeneous catalyst particle in a reactor, and comprises the steps of: (a) allowing a reaction liquid supplied into the reactor to react in the presence of the heterogeneous catalyst particle, and (b) passing the resultant reaction liquid containing the heterogeneous catalyst particle through a line screen having an opening width where the heterogeneous catalyst particle is not allowed to pass substantially, and then extracting the reaction liquid separated from the heterogeneous catalyst particle from the reactor.

The present invention aims liquid-phase reactions, and does not aim gas-phase reactions.

The term "a line screen having an opening width where the heterogeneous catalyst particle is not allowed to pass substantially" means that the heterogeneous catalyst particle which passes through the line screen may exist in an amount which does not affect attaining functions and effects of the present invention because the heterogeneous catalyst particle as industry used has particle distribution without fail.

The opening width of the line screen is determined so that the ratio of particles which pass through the line screen can be ordinary not more than 5 volume %, preferably not more than 2 volume %, more preferably not more than 0.3 volume %.

In addition, the 15% particle diameter is defined as the diameter when the particle distribution in terms of volume becomes 15% at the small particle side, and it is effective that the opening width of the line screen is determined narrower than the above 15% particle diameter. The lower limit of the opening width of the line screen can be determined in the larger size of ½₅ of the 15% particle diameter or 0.05 mm. In case where the opening width is narrower than the above size, there are disadvantages in long-time operation because the screen is easily clogged with even a small amount of such as small fragment of the catalyst particle, and the screen filled with the small fragment in the above way is with difficulty washed.

These and other objects and the advantages of the present invention will be more fully apparent from the following detailed disclosure.

EXPLANATION OF THE SYMBOLS

Figure 1:
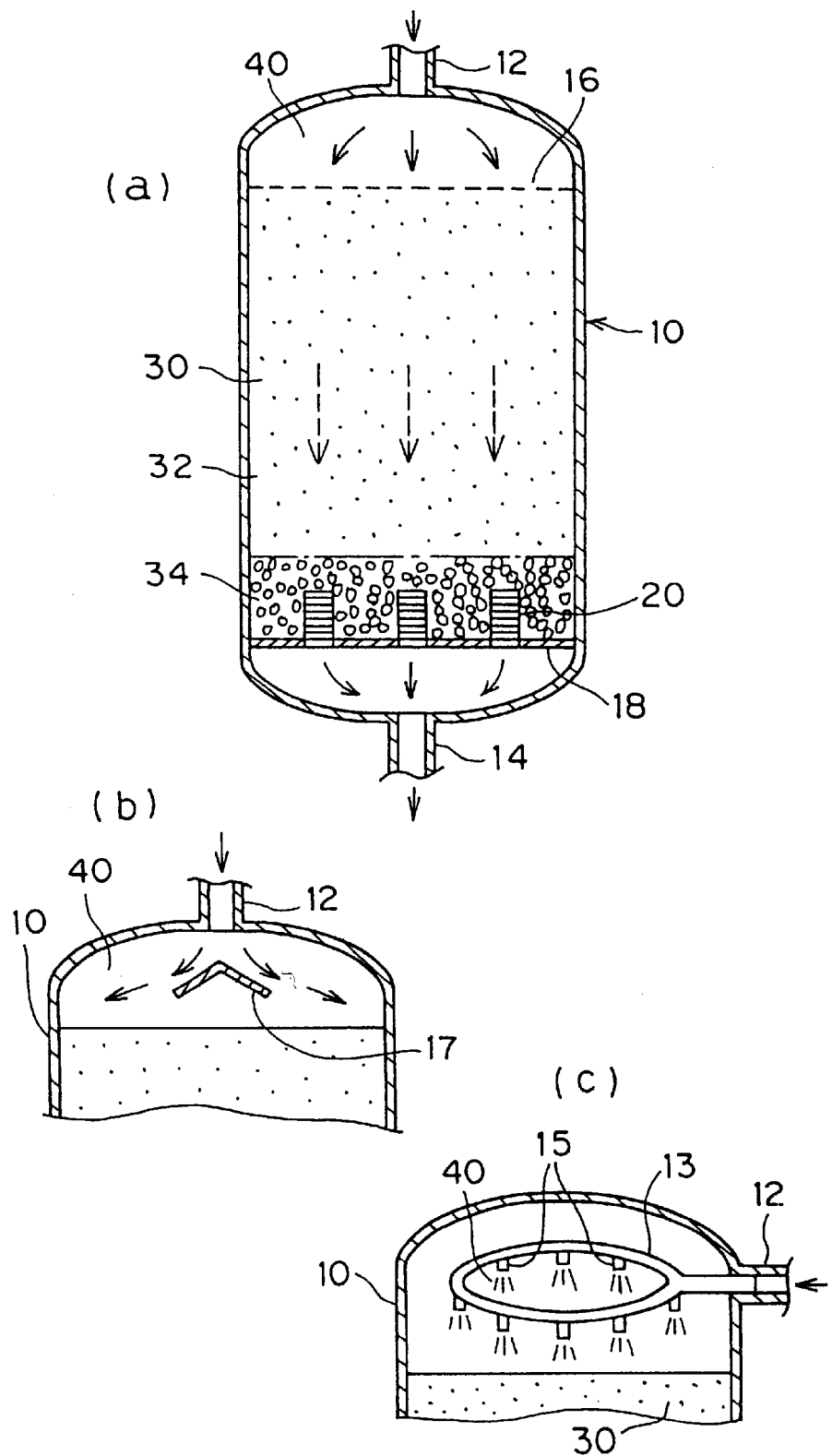
FIG. 1 is a sectional view (a), and major sectional views (b) and (c) of a fixed bed reaction apparatus representing a mode for carrying out the present invention.

10, 50: Reactor
12: Supply inlet
14: Liquid-extracting outlet
15: Liquid-flowing inlet
16: Distributing plate
18: Partition plate
20: Solid-liquid separator
21: Opening
22: Line material
30: Homogeneous catalyst particle
40: Reaction liquid
52: Stirrer

DETAILED DESCRIPTION OF THE INVENTION

Hereinafter, the modes for carrying out the present invention are explained in detail.

[Average Particle Diameter]

In the present invention, the usable heterogeneous catalyst particle has an average particle diameter of 0.1 to 3 mm. The average particle diameter is defined as 50% particle diameter, and the measurement method thereof is in the same method as of the 15% particle diameter. However, the evaluation standard is settled in 50%. In case where the particle diameter of the heterogeneous catalyst particle exceeds 3 mm, the contact area with the reaction liquid decreases and the reaction efficiency lowers. On the other hand, in case where the particle diameter of the heterogeneous catalyst particle is smaller than 0.1 mm, the clogs are easily caused when the heterogeneous catalyst particle and the reaction liquid are separated. The average particle diameter of the heterogeneous catalyst particle is more preferably in the range of 0.3 to 2 mm. Incidentally, the particle diameter of the heterogeneous catalyst particle can be measured by such as: measurement with micrometers, vernier calipers, ultrasonic measurement apparatuses, or optical microscopes; a method which involves obtaining microscopic images and calculating with an image-processing apparatus and a computing apparatus; or classification by sieves.

[15% Particle Diameter]

When the particle diameter of the heterogeneous catalyst particle is defined as the above 15% particle diameter, the particle diameter can be measured by the below method.

For example, in case that the particle is in a moist state, the volume is measured by use of such as a measuring cylinder in a state that the resin particle is immersed and sedimented in a liquid which can possibly have the same component as of the solvent which moistens the particle (concretely, the volume is when the volume is not decreased any more while tapping the bottom). While the same particle mildly flows with the same liquid, the particle is separated into a passed fraction and an on fraction by use of a measuring sieve of which mesh is accurately determined. The passed fraction and on fraction are collected respectively, and the volume is measured with a measuring cylinder. Then, the passed fraction is less than 15 volume %, it is understood that the 15% particle diameter of this particle is larger than the mesh of the sieves. The 15% particle diameter of the particle can be measured by repeating the above measurement with changing the mesh.

When it is difficult to handle in the same component or at the same temperature as of the solvent which moistens the particle, the solvent such as water may be replaced to measure. However, it is preferable to adjust the resin volume change caused by the replacement of the solvent in the range of not more than ±10%.

In case where the resin volume change of the heterogeneous catalyst particle is not more than ±10% between the moist state and the dry state, the 15% particle diameter may be defined with the particle in the dry state. In this case, it is not necessary to use the liquid. The size of the particle compared with the mesh may be evaluated by whether or not the passed fraction is not more than 15 volume % when the particle is separated by use of a vibration sieve.

[Heterogeneous Catalyst]

The heterogeneous catalyst as used in the present invention is not especially limited.

Examples thereof include all the ion-exchange resins which are ordinary commercially available, such as strong or weak acidic cation-exchange resins, and strong or weak basic anion-exchange resins. Particularly, when using the resins in the exothermic reaction, the resin having heat resistance is preferable. Examples of the heterogeneous catalyst except for the ion-exchange resin include: metal, noble metal, or oxides thereof; ceramics such as silica, alumina, and titania, or active carbon, which contains such as metal, noble metal, or oxides thereof.

The shape of the heterogeneous catalyst is not especially limited, but usable examples thereof include spheres, elliptic spheres, pelletized columns, quadrangular pyramids, circular cones, and needles. Spheres or elliptic spheres almost spheres is preferable because of easily flowing at agitation or preventing the resin from rushing due to collision of each resin particle.

[Cation-exchange Resin]

Particularly, the strong acidic cation-exchange resins can preferably be used as acidic cation-exchange resins. The usable resins are porous or gelled resins.

Examples of the porous strong acidic cation-exchange resins include: MSC-1 (above, Dow); PK-208, PK-212, PK-216, PK-220, and PK-228 (above, Mitsubishi Chemicals); AMBERLYST-16, IR-116, IR-118, IR-122, C-26, C-26TR, C-264, and C-265 (above, Rohm and Hass Company); SPC-108 and SPC-112 (above, Bayer); and KC-470 (Sumitomo Chemical).

Examples of the gelled resins include: HCR-S, HCR-W2, and HGR-W2 (above, Dow); and SK-1B, SK-106 and SK-110 (above, Mitsubishi Chemicals).

[Anion-exchange Resin]

Either the strong or weak basic anion-exchange resins can be used as basic cation-exchange resins. When the resins are used for an addition reaction of alkylene oxide in the present invention, the strong basic anion-exchange resins are preferably used. In addition, either gelled, porous, macroporous, primary crosslinked or secondary crosslinked resins can be used.

Examples of the gelled resins include: SBR, SBR-P-C, and SAR (above, Dow); IRA-400, A-132, ES-137, A-101D, A-147, A-104, A-109, and A-102D (above, Rohn and Hass Company); SA10A and SA20A (above, Mitsubishi Chemicals).

Examples of the macroporous resins include: MSA-1 and MSA-2 (above, Dow); IRA-900, IRA-938, IRA-958, A-26, A-27, A-161, and A-162 (above, Rohm and Hass Company); PA306, PA308, PA312, PA316, PA318, PA406, PA408, PA412, PA416, PA418, WA30, WA20, and WK10 (above, Mitsubishi Chemicals).

There are weak basic resins whose kind of amino group as used as a functional group is dimethylamine among the weak basic anion-exchange resins.

Examples of the strong basic anion-exchange resins include type (I) hose kind of amino group as used as a functional group is trimethylammonium group, and type (II) whose kind of amino group as used as a functional group is dimethylethanol ammonium group.

[Suspension and Dispersion]

In the present invention, the reaction can be carried out by suspending and dispersing the above heterogeneous catalyst particle in the reaction liquid as the fluidized bed reaction method. Therefore, as soon as the reaction efficiency can be improved by increasing the frequency of contact with the heterogeneous catalyst particle and the reaction liquid, the effects of removing heat can be expected in case of using jackets and/or coils in the exothermic reaction. When it is difficult to remove heat by the jacket only, it is effective that the heat-removing ability can be raised by use of such as wound coils and hairpin coils.

The means of suspending and dispersing the above heterogeneous catalyst article into the reaction liquid is not especially limited. For examples, a method which involves using a stirrer comprising such as a paddle blade, a Pfaudler blade, a max blend blade, and an anchor blade, a method which involves introducing a gas from the bottom of the reactor, or the combination of these methods can be employed.

[Change Amount of Heterogeneous Catalyst Particle]

In case of the fluidized bed reaction method, the changing amount of the above heterogeneous catalyst particle is preferably in the range of 0.05 to 1.0 time of the entirety of the charged amount in terms of volume.

In case where the charging amount of the above heterogeneous catalyst particle exceeds 1.0 time of the entirety of the charged amount in terms of volume, there are disadvantages in that: it becomes difficult to suspend and disperse the particle, and the stir-mixing becomes uneven. In addition, there are disadvantages in that: the crush of the particle exceedingly proceeds in the neighborhood of the stirrer, and the catalyst life shortens. Bad influences such as causing the clogs of crushed particles in the latter process while operating the apparatus are exercised. The tendency of increasing a harmful side reaction is also caused.

When the volume of the heterogeneous catalyst is changed with the passage of time, the change of volume is considered and the charging amount is determined so that the charging amount can possibly be inhibited in the above range.

In case where the charging amount of the above heterogeneous catalyst particle is less than 0.5 time, there are disadvantages in that: the side reaction without catalysts in the liquid proceeds more frequently than the main reaction carried out on the catalyst surface, and the selectivity is lowered. In addition, the promotion of the reaction needs to stir strongly. Therefore, the catalyst is easily crushed.

[Blade Tip Speed]

When the reaction is carried out in the reaction vessel comprising the stirrer by stirring the reaction liquid, the tip speed of the stirring blade of the stirrer is desirably determined in the range of 0.1 to 10 m/s, preferably 0.3 to 5 m/s.

The tip speed of the stirring blade of the stirrer is calculated from the up span of the stirring blade and the stirring rotation number according to the below equation.

$$\text{The tip speed of the stirring blade (m/s)} = \text{the span (m)} \times \text{the stirring rotation number (rpm)} \times \pi/60$$

In case where the tip speed of the stirring blade exceeds 10 m/s, it is not economical because the apparatus cost for stirring and the running cost of motive power become enormous. In addition, the power is exceedingly added to the heterogeneous catalyst particle, and then the heterogeneous catalyst particle is injured and crushed. Therefore, there are disadvantages in that: the catalyst life shortens, and the trouble is easily caused due to the crushed materials in the latter process.

On the other hand, in case where the tip speed of the stirring blade is slower than 0.1 m/s, there are disadvantages in the reaction because it is difficult to float the heterogeneous catalyst particle in the reaction liquid, the reaction partially becomes heterogeneous, the ununiformity of temperature or concentration is locally caused, and the side reaction increases. In addition, there are disadvantages in controlling the reaction temperature because the heat-removing efficiency lowers when removing reaction heat.

[Reaction Temperature]

The reaction is preferably carried out in the condition of the reaction temperature adjusted in the range of 15 to 120° C.

In case where the reaction temperature is higher than 120° C., there are disadvantages in that: dimer acids or oligomers increase, and further, the side reaction for producing esterified products thereof and products having high boiling point. In addition, there are disadvantages in that the trouble is easily caused due to the polymerized products.

In case where the reaction temperature is lower than 15° C., there are disadvantages in that the cost of cooling refrigerant for cooling increases. In addition, there are many demerits in economy because the reaction rate is frequently slow, and the size of the apparatus becomes large.

The reaction can preferably be employed in the range of 30 to 115° C., more preferably 50 to 105° C.

Incidentally, the reaction condition except for the above way is not especially limited in the present invention, and is fitly determined according to the conventional arts.

[Separation of Solid and Liquid]

In the present invention, after the reaction in the presence of the heterogeneous catalyst particle, the reaction liquid containing the heterogeneous catalyst particle is passed through a line screen having function of separating solid and liquid. Therefore, the reaction liquid and the heterogeneous catalyst particle are separated, and then the reaction liquid is extracted from the reactor.

The line screen has many line materials which are placed on parallels at a predetermined interval. Support part materials might also be placed perpendicular to the line materials. Even in this case, the line is substantially formed by determining the placing interval of the supporting part materials enough larger than the opening width of the line materials each other.

It is preferable to use the line screen of which opening width of the line materials each other comprising in the line screen is substantially narrower than the particle diameter of the heterogeneous catalyst particle. The heterogeneous catalyst particle and the reaction liquid can be certainly separated because the above opening width is narrower than the particle diameter of the heterogeneous catalyst particle. In addition, it becomes difficult to cause the clogs of the heterogeneous catalyst particle, and the stable operation can be carried out for a long time by separation of solid and liquid with the screen comprising the line material. The mesh opening of the line screen can be uniformly controlled at a certain interval, and the portion having an opening width narrower than the designed size is little. Therefore, it is preferable that the clogs are difficult to cause because an extremely small particle contained in the heterogeneous catalyst particle is passed through the screen.

The ratio of maximal and minimal values of the mesh opening scatter of the screen is preferably determined in the range of not more than two times. In case where this ratio exceeds two times, the heterogeneous catalyst particle is easily leaked and the clogs are easily caused at a narrow portion of the opening. The ratio is preferably determined in the range of 1.0 to 1.5 times, more preferably 1.0 to 1.2 times. Incidentally, the minimal value herein is evaluated by excluding structurally and locally narrow portions such as a connecting portion to the screen.

The line screen is not especially limited if it comprises the line material. Examples thereof include: mesh or lattice plates, mesh cylinders, coils, and plates obtained by placing straight lines parallel; plane materials obtained by helically coiling lines, and placing them along plane circle; plane materials obtained by processing lines into plural circles having a different diameter, and placing them along circles which are at a predetermined interval and have the same center, and further, plate materials obtained by processing lines into similar multiangular figures having a different size, and placing the multiangular figures to adjust their respective centers. If the line screen is a plate, the structure thereof can be made simple. The line screen is effective if the effective area for separating solid and liquid is even little but good. If the line screen is a cylinder or a coil, it is preferable because the effective area for separating solid and liquid can take up much space and the line screen is easy to remove.

The cross sectional shape of the line material as comprised in the line screen is not especially limited, but examples thereof include circles, ellipses, triangles, quadrilaterals, and trapezoids. Circles, ellipses, triangles, and trapezoids are preferable. If the shape is a triangle or a trapezoid and the wide base side is placed at the inlet side for separating solid and liquid, there are advantages in that the flow goes wide toward direction of the liquid flow. If the narrow base side is toward the inlet side for separating solid and liquid, the flow goes narrow toward direction of the liquid flow at the opening between neighboring line materials. Therefore, there are disadvantages in that it is easy to clog with the particle.

In addition, the opening width of the respective line materials is, for example, preferably in the range of 0.05 to 2 mm. The size of width of the respective line materials in the longitudinal direction is not substantially limited if it is enough longer than the opening width. For example, if the structure is that the line material is helically coiled, the length of the opening width can be freely extend. However, when the supporting part materials are placed perpendicular to the line materials, the intervals of the supporting part materials can be evaluated as the substantial length of the opening and determined in the range of not less than 5 times length based on the opening width. The upper limit of the length is not especially limited if the limit is length which enables to place the supporting part materials in the range where the mesh is not ununiform and where the line materials are not distorted forcibly due to such as liquid pressure and pressure difference. The actual upper limit of the length is in the range of several tens centimeter to 1 meter.

In the present invention, the means of passing the reaction liquid containing the heterogeneous catalyst particle through the above line screen and extracting the reaction liquid from the reactor is not especially limited, but for example, the pressure of the reactor side of the above line screen is preferably adjusted higher than the pressure of the side where the reaction liquid is extracted.

[Specific Gravity]

The reaction method according to the present invention can display effects in particular when the specific gravity of the above heterogeneous catalyst particle in a state of absorbing the reaction liquid is in the rage of 0.9 to 2.0 times based on the specific gravity in the reaction liquid containing the heterogeneous catalyst particle. This range of the specific gravity enables to separate solid and liquid with a more compact apparatus than a liquid cyclone or a gravity sedimentation known as a conventional means of separating solid and liquid. Needless to say, even if the specific gravity of the above heterogeneous catalyst particle based on the specific gravity of the reaction liquid is outside the above range, the reaction method according to the present invention can be applied.

Incidentally, the specific gravity can be measured in the following way.

The specific gravity of the particle in a moist state is defined as (weight g obtained by excluding space portion of the particle in a moist)/(volume $cm^3$ in the above state).

As to the exemplified measurement method, a liquid and a resin are accurately weighed with a measuring cylinder so that that liquid and particle surfaces of the moist sample can match at 10 $cm^3$. The weight ($W_1$) of the sample is measured. The sample resin is wrapped with cloth or vinyl sponge, and filtrated with a centrifuge over a period of about 5 to 10 minutes in order to separate the liquid and the resin. Then, the resin is transferred into a weighing bottle, and the bottle is sealed, thus measuring the weight ($W_2$) of the resin after extruding liquid-adding portion. The centrifuge may be operated in a diameter of about 15 cm at about 3,000 rpm. The specific gravity γ of the liquid is measured beforehand. The space gravity is calculated according to the below equation from the measured result.

$$\text{Specific gravity in a most state } (g/cm^3)=W_2/[10-(W_1-W_2)\gamma]$$

[Exothermic Reaction]

The reaction method according to the present invention can fitly be applied to the reaction to generate a calorific value of 0.1 to 3,000 kcal/h/kg based on the liquid amount in the reactor. Generally, when carrying out the exothermic reaction, the trouble is easily caused due to the locally heat generation or side reaction at a piling portion of the heterogeneous catalyst particle or the reaction liquid. Therefore, the present invention which can solve these problems is effective.

In case where the calorific value of the reaction exceeds 3,000 kcal/h/kg and the piling portion is caused while separating the heterogeneous catalyst particle and the reaction liquid, higher heat generation is partially caused. The heat cannot often be removed even if refrigerant is used. Then, the partial heat generation causes inconveniences such as polymerizing the reaction product and shortening the life of the heterogeneous catalyst particle. In the present invention, the piling portion is not caused while separating the heterogeneous catalyst particle and the reaction liquid, and these problems can easily be avoided. Especially, the above problems can effectively be avoided in case of the fluidized bed. Incidentally, the calorific value as generated in the reaction can be forecasted from the theoretical calorific value per 1 mol of the major reaction raw material (among the reaction raw materials, based on the material having the smallest molecular weight). When the theoretical calorific value per 1 mol of the major reaction raw material is in the range of 5 to 50 kcal/mol, the reaction method according to the present invention may be applied.

Needless to say, even if the calorific value of the reaction is less than 0.1 kcal/h/kg and if the present invention is applied, the piling portion of the heterogeneous catalyst particle and the reaction liquid can be little. Therefore, it is effective in inhibiting the side reaction

[Reaction Method]

The reaction method according to the present invention is not especially limited if the reaction method involves carrying out the reaction in liquid phase by using the heterogeneous catalyst particle, and can be applied to various reaction methods. Especially, the reaction method is effective for reactions to treat polymerizable materials such as a reaction using (meth)acrylic acid. Examples of the reaction using (meth)acrylic acid include a reaction to produce (meth)acrylate. In addition, the examples also include a reaction to purify (meth)acrylic acid and/or its esters by allowing aldehydes in impurities contained in (meth)acrylic acid and/or its esters to react with a compound having at least one mercapto group in a molecule, such as mercaptan, in the presence of an ion-change resin.

Examples of the reaction to produce (meth)acrylate preferably include: a reaction to produce (meth)acrylate by allowing (meth)acrylic acid to react with an alcohol; and a reaction to produce hydroxyalkyl (meth)acrylate by allowing alkylene oxide to react with (meth)acrylic acid. In this reaction to obtain the hydroxyalkyl (meth)acrylate, the calorific value during the reaction is large and the polymerizability of the hydroxalkyl (meth)acrylate as obtained is very high among them. Therefore, it is thought that the effect is especially large when the method according to the present invention is used.

The (meth)acrylates are preferably treated in the presence of general polymerization inhibitors or stabilizers in order that the present invention can be more effective. The above additives are not especially limited if they are substances which have polymerization-inhibiting effects.

<Reaction to Produce (Meth)acrylate by Allowing (Meth)acrylic Acid to React With Alcohol>

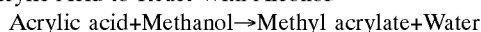

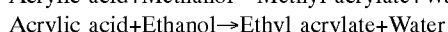

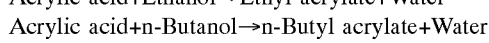

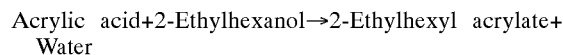

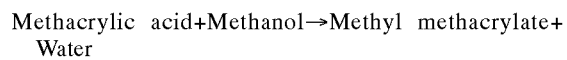

In these reactions, the activity and selectivity can be improved by equipping such as reactors with a dewatering column to remove water.

<Reaction to Produce Hydroxyalkyl (Meth)acrylate by Allowing Alkylene Oxide to React With (Meth)acrylic acid> (Exothermic Reaction)

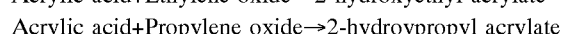

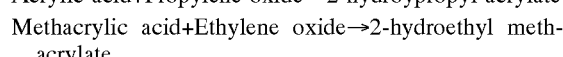

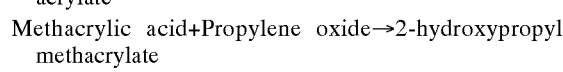

<Raw Alcohol>

Methanol, ethanol, propanol, butanol, isobutanol, tert-butyl alcohol, and 2-ethylhexyl alcohol can be used.

<Raw Acid>

(Meth)acrylic acid is used.

<Raw alkylene Oxide>

Ethylene oxide, propylene oxide, butylene oxide, and styrene oxide can be used.

The reaction method according to the present invention may be carried out by dividing two or more steps. For example, the reactivity and selectivity can be improved by: extracting the resultant reaction liquid in which the reaction goes on to a certain extent as mentioned above, and allowing the resultant reaction liquid as extracted to react further in the same way.

[Reaction Apparatus]

The reaction a apparatus, according to the present invention, is an apparatus for the reaction by using the above heterogeneous catalyst particle. Both fixed bed reaction apparatus and fluidized bed reaction apparatus can be applied. The apparatus comprises a vessel-type reactor equipped with a stirrer, and a liquid-extracting line. The apparatus comprises a line screen which is placed between the reactor and the liquid-extracting line and has function of separating solid and liquid. The line screen has an opening width where the heterogeneous catalyst particle is not allowed to pass substantially.

The line screen is preferably attached to a side-wall of the reactor so that the screen surface of the line screen can face inside downward. The clogs with the heterogeneous catalyst particle can effectively be prevented because the screen is placed so that the screen surface can face downward in this way.

Furthermore, in case of the fluidized bed reaction apparatus, the line screen is preferably placed not to greatly prevent a reaction liquid slurry including the heterogeneous catalyst particle from flowing while separating solid and liquid.

The reaction apparatus, according to the present invention, preferably comprises the above plural liquid-extracting lines, and the respective lines are connected to the above reactor through different line screens.

The efficiency for separating solid and liquid rises, and troubles decreases because the line screen is settled in the flowing route of the reaction liquid. The concrete place to be settled is not especially limited.

For example, a nozzle may be attached to the bottom of the vessel and the nozzle may be filled with the line screen or the line screen can be attached so that the line screen can be protruded from the nozzle. The plain screen can be attached to the bottom of the vessel. A nozzle can be attached to the side of the vessel, wherein the nozzle is filled with the line screen or the line screen is attached to the nozzle with protruding partially from the nozzle. An extracting line can be attached to the upper portion of the vessel, and the line screen can be placed at its tip.

However, in case of the fluidized bed reaction apparatus, when the line screen is placed at the piling portion of the resin, troubles are easily caused due to going on side reaction at the piling portion or solid materials such as polymerized products. Therefore, the line screen is preferably placed at a liquid-flowing portion due to each agitation or circulation.

When the line screen is placed at the piling portion, there are demerits that the heterogeneous catalyst resin particle is attached to the screen surface and the pressure difference of filtration rises at a rate of the attachment. However, when the line screen is placed at the liquid-flowing portion, the pressure difference of filtration does not rise. This reason is considered that the heterogeneous catalyst particle is always washed away and is not piled on the surface. Troubles such as side reaction and polymerization due to ping the heterogeneous catalyst are also removed.

If the liquid is in a flowing state, a basket which enters into the reactor is made of the line screen, and the reaction can be carried out while the heterogeneous catalyst and the stirrer in this basket and the catalyst is stirred.

In case of the fixed bed reaction apparatus, its fundamental structure is also common to that of the fluidized bed reaction apparatus. The same art can also be applied to the structure of the line screen. The line screen can be placed so as to constitute a flat surface crossing the reactor. The line screen can be placed on the whole or part of the cross vertical section.

The position of the line screen may be placed so as to obtain a uniform flow toward the vertical cross section against the liquid-flowing direction in the reactor of the fluidized bed reaction apparatus. For example, if the screen is a cylindrical screen, not less than 3 pieces of it per 1 $m^2$ may uniformly be placed toward the vertical cross section against the liquid-flowing direction. In case where less than 3 pieces of it per 1 $m^2$ are placed, there are disadvantages in that: the piling portion of the liquid is caused in the catalyst layer, polymerized products are easily produced; the screen is clogged; and the reaction efficiency is lowered.

The reactor of the fixed bed reaction apparatus is fix-packed with a heterogeneous catalyst. The method and condition for packing the heterogeneous catalyst can be performed in the same way as of conventional reaction methods.

The reaction liquid can flow upward from the lower side to the up side of the reactor, or flow downward from the upper side to the lower side. In case of reaction distillations which involves separating low-boiling-point-having materials, such as esterifying reaction or transestrification, the reaction liquid preferably flows upward. In case of inhibiting clogs, the reaction liquid preferably flows downward.

In the reactor, the heterogeneous catalyst article having a comparatively larger diameter can be placed at a position adjacent to the line screen, and the heterogeneous catalyst particle having a comparatively smaller diameter can be placed at a position apart from the line screen. The heterogeneous catalyst particle having a comparatively larger diameter is difficult to pass through the opening of the screen. The heterogeneous catalyst particle having a comparatively smaller diameter has good reaction efficiency. The heterogeneous catalyst particle having a comparatively larger diameter functions as a screen which prevent the heterogeneous catalyst particle having a comparatively smaller diameter from passing through.

When the flat line screen is placed at the bottom side of the reactor, the upper space of the line screen can be packed with the heterogeneous catalyst particle having a comparatively larger diameter in definite depth, and the further upper space can be packed with the heterogeneous catalyst particle having a comparatively smaller diameter.

As to the diameter ratio of the above two kinds of heterogeneous catalyst particles, the diameter of the heterogeneous catalyst particle having a comparatively smaller diameter can be adjusted to about 0.8 time of that of the heterogeneous catalyst particle having a comparatively larger diameter. The diameter of the heterogeneous catalyst particle having a comparatively larger diameter can be adjusted to the range of 1.1 to 30 times of the opening width of the line screen, and the diameter of the heterogeneous catalyst particle having a comparatively smaller diameter can be adjusted to the range of 1.0 to 15 times of the opening width of the line screen.

Furthermore, a comparatively larger particle having no catalytic function can be placed at a position adjacent to the line screen, and the heterogeneous catalyst particle having a comparatively smaller diameter can be placed outside it. As an example of the particle having no catalytic function, stainless steel can be used.

In the reactor, a distributing plate having such as mesh can be placed at a side when the reaction liquid is supplied in order to prevent the heterogeneous catalyst particle from reversely flowing or to improve distributing the reaction liquid. The reaction liquid preferably distributes toward the horizontal cross section of the packed layer of the heterogeneous catalyst as uniformly as possible.

When the reaction liquid flows downward, the countermeasure of reversely flowing of the heterogeneous catalyst particle is not always necessary. Then, the distributing plate to improve distributing the reaction fluid does not always have to cover fully. The distributing plate may be a perforated plate, or perforated plate with umbrella shape placed fully or partially. The plate can be replaced with a comparatively smaller one in consideration of maintenance. The shape or structure of the distributing plate is not especially limited if the liquid is distributed on the heterogeneous catalyst particle by applying to conventional distributing methods.

[Examples of Reaction Apparatus]

Hereinafter, the reaction apparatus of the present invention as used in the reaction by use of the above ion-exchange resin is explained with figures.

<Fixed Bed Reaction Apparatus (1)>

The reaction apparatus represented in FIG. 1(*a*) is a fix bed reaction apparatus.

The cylindrical reactor 10 of which cross section is circular and of which upper and lower ends are dome-shaped and clogged comprising a supplying inlet 12 of the reaction liquid 40 at the upper end, and a liquid-extracting outlet 14 to extract the resultant reaction liquid at the lower end.

A mesh-shaped distributing plate 16 is placed near the upper portion of the inner space of the reactor 10, and a partition plate 18 is placed near the bottom portion. The space between the distributing plate 16 and the partition plate 18 is packed with the heterogeneous catalyst particle 30. The partition plate 18 comprises a solid-liquid separator 20 having a cylindrical line screen. The reaction liquid 40 passes through the solid-liquid separator 20, and is sent out to the lower space of the partition plate 18.

The definite depth of the lower side near the partition plate 18 and the solid-liquid separator 20 is packed with a heterogeneous particle 34 having a comparatively larger particle diameter. The solid-liquid separator 20 is in a state of filling with the heterogeneous particle 34 having a comparatively larger particle diameter. The upper portion of the heterogeneous particle 34 having a comparatively larger particle diameter is packed with a heterogeneous particle 32 having a comparatively smaller particle diameter.

The reaction liquid 40 is supplied to the reactor packed with the heterogeneous catalyst particle 30. Therefore, the reaction liquid 40 is fully and uniformly spread above the reactor 10 by the distributing plate 16, flows downward in the reactor 10, and the reaction is caused in the presence of the heterogeneous catalyst particle 30. The resultant reaction liquid 40 is separated from the heterogeneous catalyst particle 30 with the liquid-solid separator 20, and only the reaction liquid 40 is extracted from the liquid-extracting outlet 14.

When the distributing plate 16 does not exist, the reaction liquid 40 intensively flows into the central portion of the reactor 10 lying right beneath the supplying inlet 12. Therefore, the ratio of portion utilized effectively for the reaction among the capacity of the reactor 10 lowers and the reaction efficiency becomes easily deteriorated. Particularly, the reaction liquid is easily piled around the portion near the upper end of the reactor 10, and the polymerization or side reaction is easily caused. The distributing plate 16 is effectively placed to solve such a problem In addition to the mesh-shaped distributing plate 16 represented in FIG. 1(a), a perforated distributing plate can be used, and an umbrella distributing plate 17 can be placed right beneath the supplying inlet 12 as shown in FIG. 1(b). The plural distributing mans can be placed in combination with each other.

Incidentally, in addition to the structure that only the one supplying inlet 12 is placed right over the reactor 10, the plural supplying inlets 12 can also be placed dispersingly and fully over the surface of the reactor 10.

Furthermore, as is represented in FIG. 1(c), if placing a liquid-flowing inlet 15 which is connected to the supplying inlet 12 in the reactor 10 and comprises a short tube or a penetrated opening at the plural portions of a distributing piping tube 13 which is circularly shaped overall, the reaction liquid 40 can be distributed and supplied uniformly in the circular direction. As is omitted to represent figures, if the same as of the above distributing piping tube 13 is placed at a side adjacent to the liquid-extracting outlet 14 at the lower portion of the reactor 10, the reaction liquid 40 which passed through the solid-liquid separator 20 can be collected uniformly from all the circular portions and sent out to the liquid-extracting outlet 14.

Figure 2:
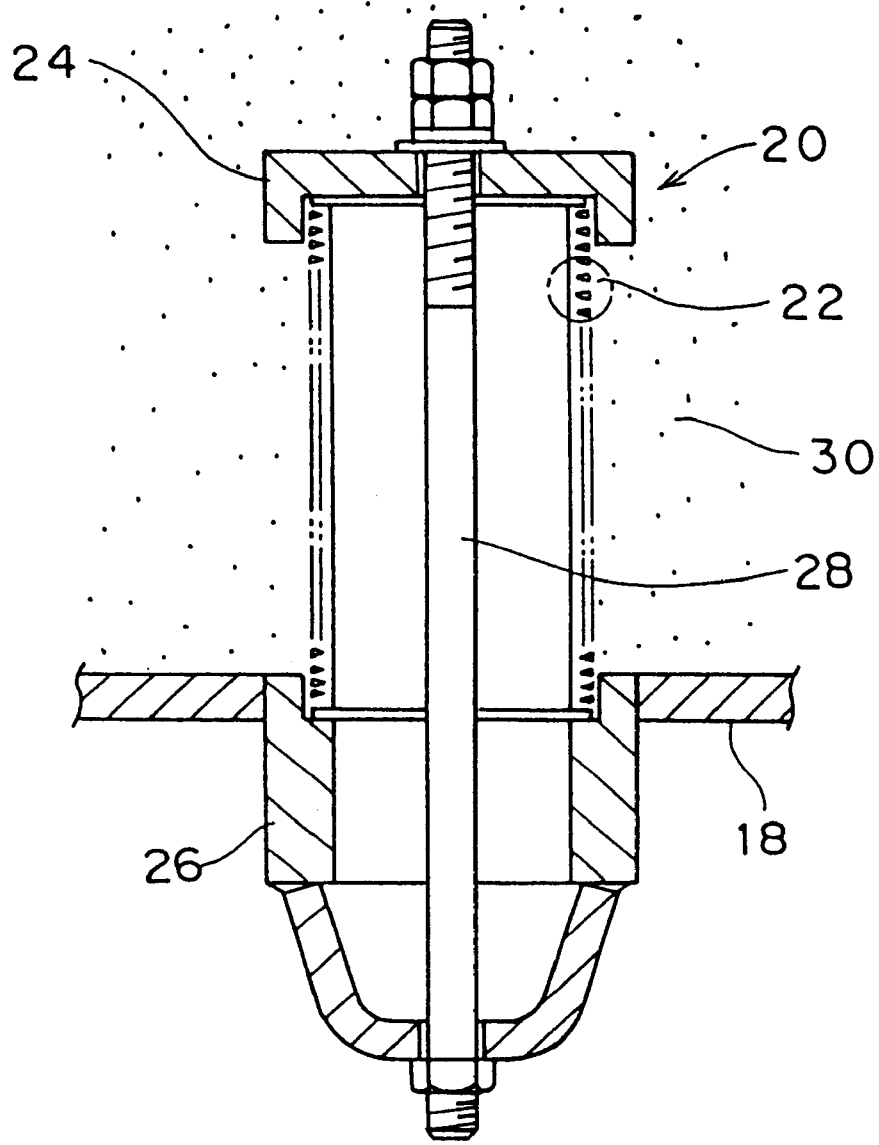
FIG. 2 is an expanded sectional view of a solid-liquid separator.
Figure 3:
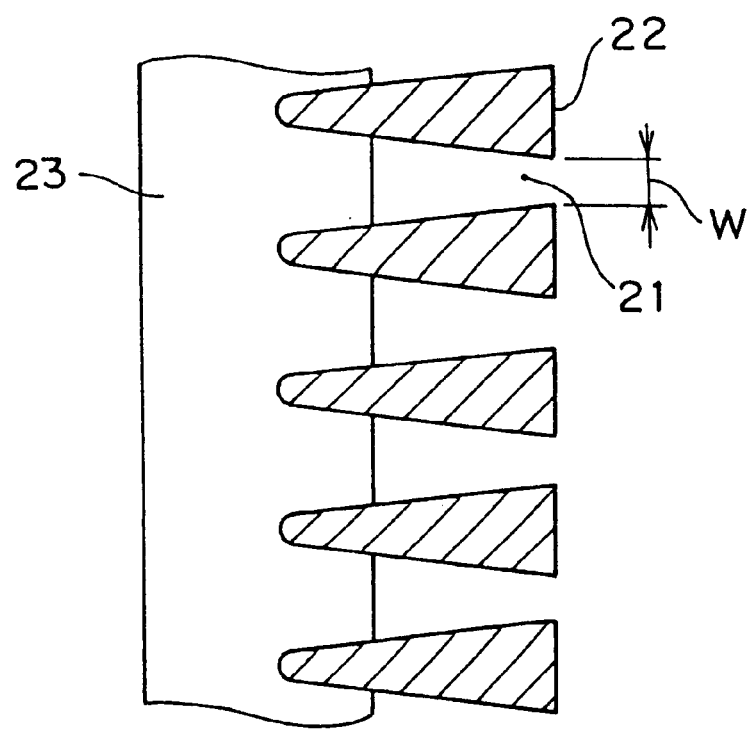
FIG. 3 is an expanded sectional view of a line screen.

FIGS. 2 and 3 represent detailed structures of the solid-liquid separator 20.

The line material 22 comprised in the line screen is helically coiled and supported in a cylindrical state. Supporting materials 24, 26 are placed over or beneath the line material 22 forming a cylindrical shape. The upper and lower supporting materials 24, 26 are supported by a supporting bolt 28 which penetrates centrally. The solid-liquid separator 20 is installed by fixing the supporting material 26 with the partition plate 18.

As is represented in FIG. 3, the line material 22 helically coiled is placed to make an opening 21 between the neighboring line material 22, and is attached to the supporting shaft 23 which is placed inside the line material 22 and supported by the upper and lower supporting materials 24, 26. The cross section shape of the line material 22 is nearly an isosceles triangle. Its wide base is placed outside, and its is placed inside.

When the reaction liquid 30 containing the heterogeneous catalyst particle 30 tries to pass through the cylindrical line screen comprising the line material 22, the heterogeneous catalyst particle 30 having a larger diameter than the width W of the opening 21 between the line materials 22 is stopped to pass through, and the reaction liquid 40 only passes. Therefore, the separation of solid and liquid is performed.

In FIG. 2, the lower end of the line screen comprising the line material 22 is placed at a lower position than the partition plate 18 inside the supporting material 26. This makes the reaction liquid 40 surely pass up to the upper surface of the partition plate 18 in order to separate solid and liquid. The reaction liquid 40 is difficult to pile near the upper surface of the partition plate 18.

The line screen, namely, the lower end of the line material 22 can be placed at the same or below position of the upper surface of the partition plate 18, or at a little higher position than the partition plate 18. However, the structure of the solid-liquid separator 20 can preferably placed not to cause the piling of the reaction liquid 40 over the partition plate 18 to the best of the ability. For example, the interval between the lower end of the above line screen and the upper surface of the partition plate 18 is preferably determined in the range of not longer than 15 mm.

Figure 4:
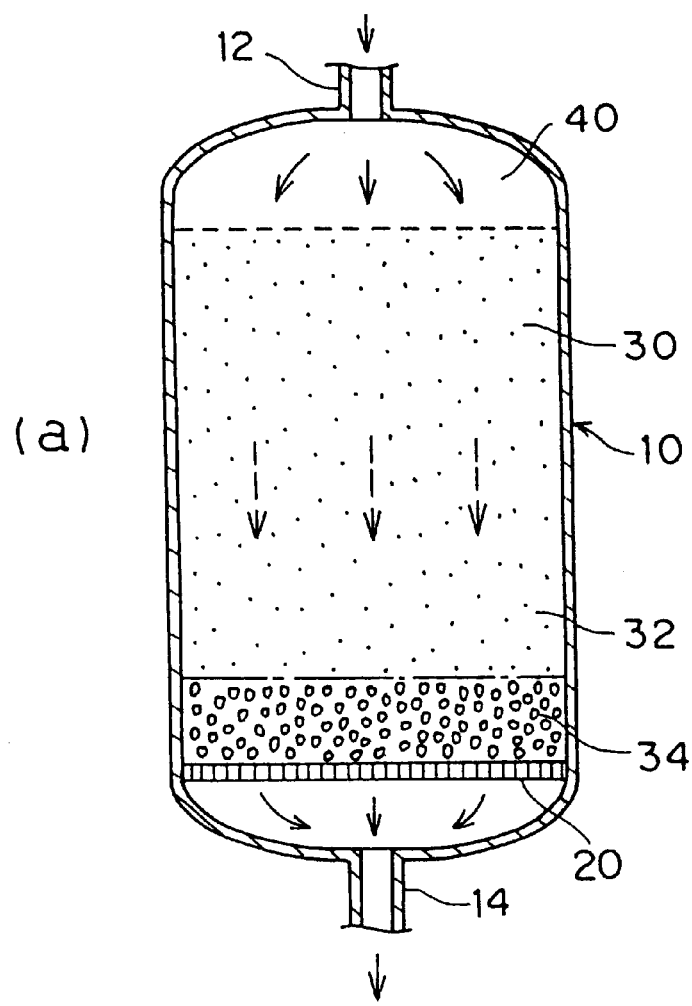
FIG. 4 is a vertical sectional view (a) and a horizontal sectional view (b) of a fluidized bed reaction apparatus.
Figure 4:
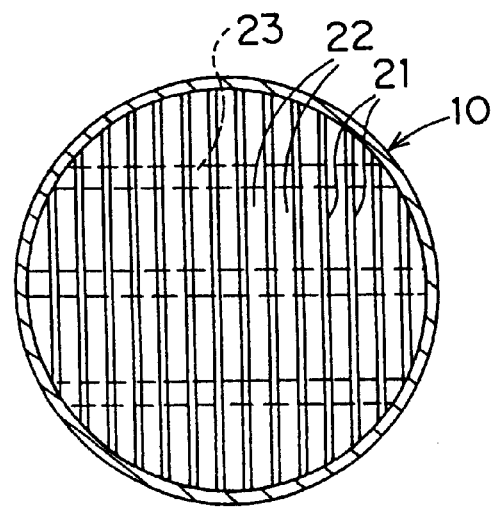

In the fixed bed reaction apparatus shown in FIG. 4, the structure of the solid-liquid separator 20 is different form the above mode for carrying out the invention.

The solid-liquid separator 20 comprising a flat line screen all over the cross section in the horizontal direction is placed near the bottom of the reactor 10. As is shown in FIG. 4(b), in the cross section of the reactor, many line materials 22 are placed parallel with making the opening 21 between each other. The cross sectional shape of the line material 22 is the same as of FIG. 3, and its wide base is placed at the upper portion, and its vertex is placed at the lower portion The many line materials 22 are supported by the supporting shaft 23 placed at the back side.

In the above mode for carrying out the invention, the whole cross section of the reactor 10 performs the function of separating solid and liquid, and the separation of solid and liquid can effectively be carried out.

<Fluidized Bed Reaction Apparatus>

Figure 5:
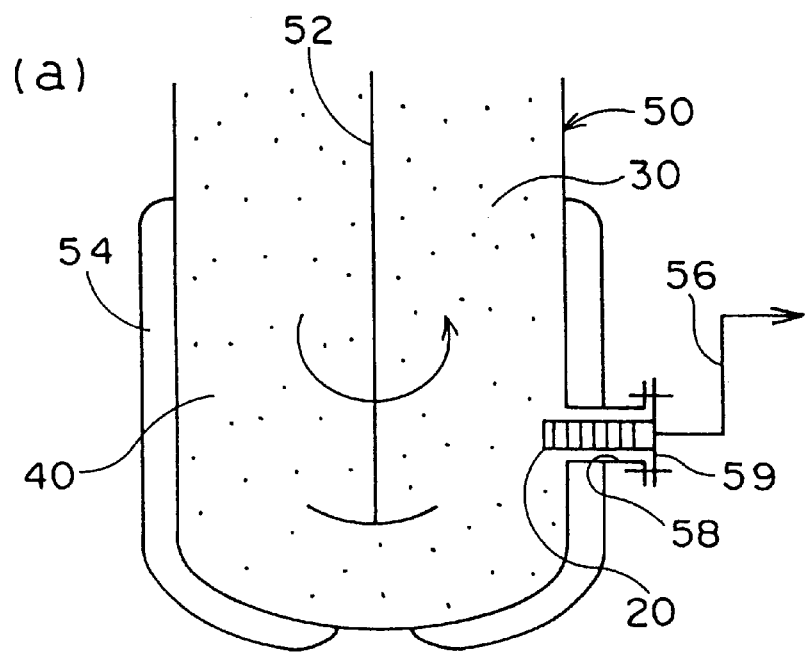
FIG. 5 is a summarized structural view (a) and a horizontal structural sectional view (b) representing another mode for carrying out the present invention.
Figure 5:
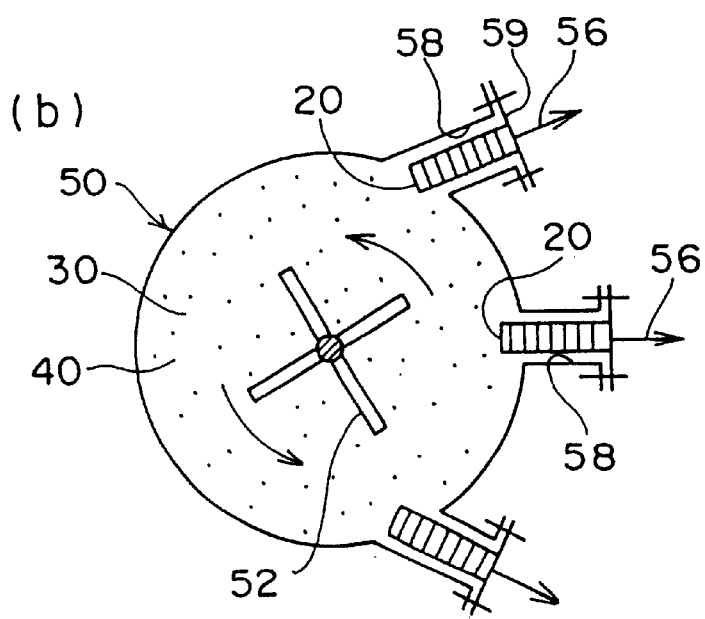

The reaction apparatus represented in FIG. 5 is a fluidized bed reaction apparatus.

The fundamental structure of the reactor 50 is the same as of the above fixed bed reaction apparatus. As is omitted to represent figures, the upper portion of the reactor 50 is equipped with a supplying inlet of the reaction liquid 40.

A stirrer 52 rotated by such as a motor is placed inside the reactor 50. A heating or cooling jacket 54 for heating or cooling is placed in outer below circumference of the reactor 50.

A solid-liquid separator 20 accommodated in an accommodation cylinder 58 is attached at the below side of the reactor 50. The solid-liquid separator 20 comprising the cylindrical line screen is connected to the liquid-extracting tube 56 which is connected to a flange plate 59 with which closes the end surface of the accommodation cylinder 58.

The most part of the solid-liquid separator 20 is placed inside the accommodation cylinder 58, and the part of the tip thereof protrudes inside the reactor 50 which is more inside than the accommodation cylinder 58.

As is shown in FIG. 5(b), the plural accommodation cylinders 58 and solid-liquid separators 20 are placed, and the materials placed in the radial direction of the horizontal cross section of the reactor 50 or the materials placed in the direction leaned toward the radial direction exist together.

In the fluidized bed reaction apparatus, the reaction liquid 40 and the heterogeneous catalyst particle 30 supplied to the upper portion of the reactor 50 are stirred with the stirred 52 to carry out the reaction in a fluidized state.

The part of the reaction liquid 40 is extracted to the liquid-extracting tube 56 by way of the solid-liquid separator 20. Then, the reaction liquid 40 alone is separated and extracted because the heterogeneous catalyst particle 30 dispersed in the reaction liquid 40 cannot pass through the opening 21 of the line material 22 comprised in the cylindrical screen of the solid-liquid separator 20.

Figure 6:
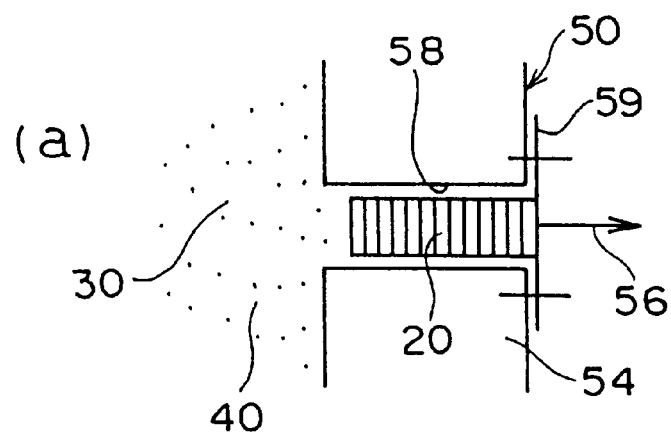
FIG. 6 is a summarized structural view representing yet another mode for carrying out the present invention.
Figure 6:
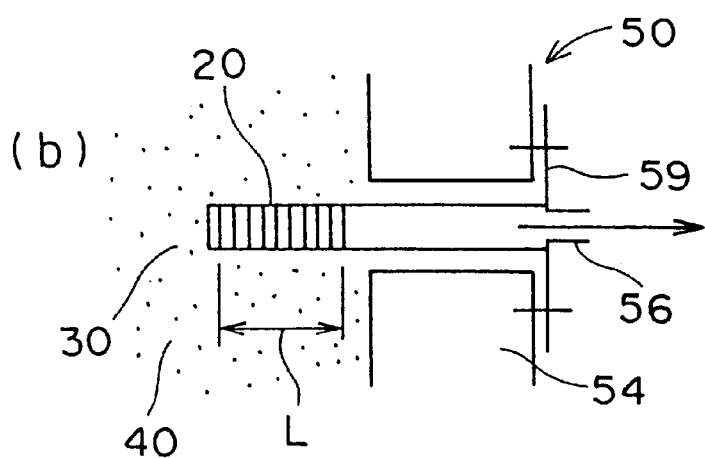
Figure 6:
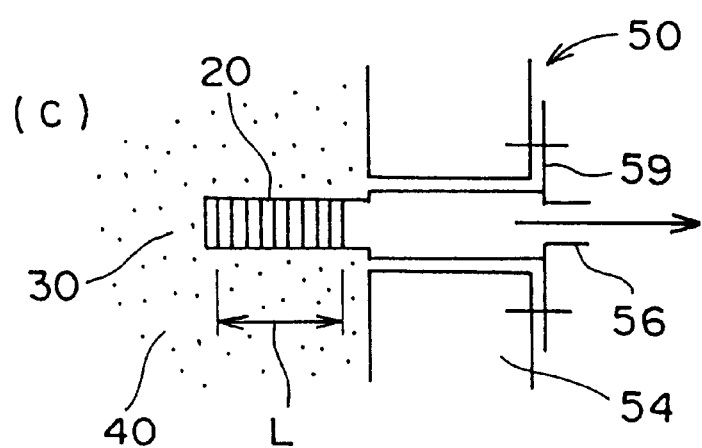

In the mode for carrying out the invention shown in FIG. 6, the structure of the solid-liquid separator 20 is different from the above mode for carrying out the invention.

In FIG. 6(a), the tip of the solid-liquid separator 20 accommodated in the accommodation cylinder 58 is placed inside the inner circular surface of the reactor 50.

In FIG. 6(b), the tip of the solid-liquid separator 20 is greatly protruded inside from the accommodation cylinder 58. In addition, the line screen comprising the line material 22 is placed only at the portion having length L of the tip side of the solid-liquid separator 20.

In FIG. 6(c), the root portion of the solid-liquid separator 20 is extended at the outer circumference so that the opening 20 between the accommodation cylinder 58 and the solid-liquid separator 20 becomes as narrow as possible in the structure of FIG. 6(b). In case of the above structure, the piling of the reaction liquid or heterogeneous catalyst particle is removed between the a accommodation cylinder 58 and the solid-liquid separator 20, and the formation of polymerized products or the side reaction can be inhibited. The opening between the accommodation cylinder 58 and the solid-liquid separator 20 may be filled with packing materials made of such as Teflon (commercial name, fluorocarbon resin).

Figure 7:
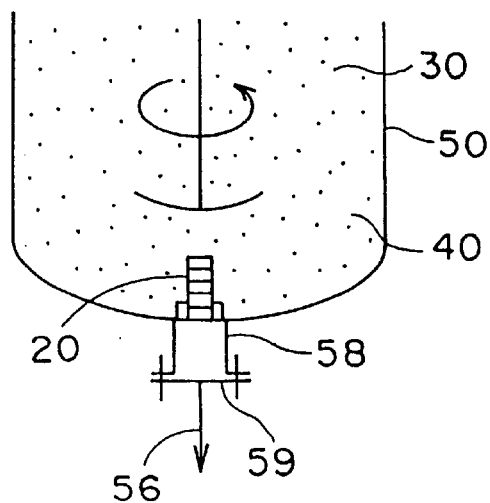
FIG. 7 is a summarized structural view representing yet another mode for carrying out the present invention.
Figure 7:
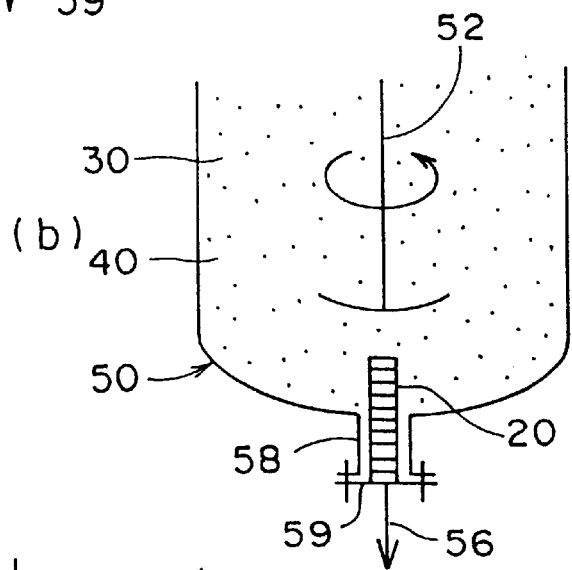
Figure 7:
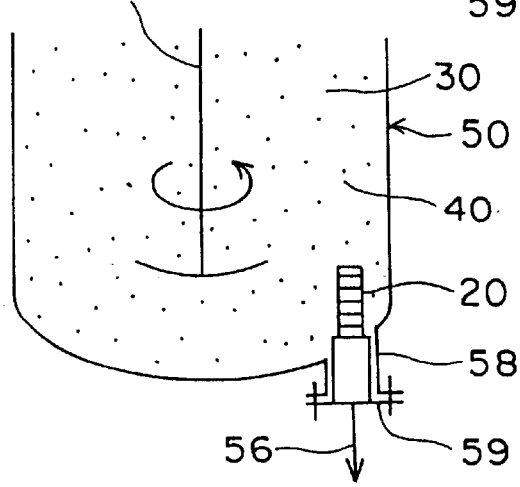

In the mode for carrying out the invention shown in FIG. 7, the solid-liquid separator 20 is placed at the center bottom of the reactor 50.

In FIG. 7(a), the solid-liquid separator 20 is placed upward at the central bottom of the reactor 50. In FIG. 7(b), the solid-liquid separator 20 is accommodated inside the accommodation cylinder 58 extended downward at the center bottom of the reactor 50. In FIG. 7(c), the solid-liquid separator 20 is placed at the circurmferential bottom of the reactor 50. The part of the solid-liquid separator 20 is placed in the accommodation cylinder 58, and the rest thereof is placed in the inner space of the reactor 50. The line screen comprising the line material 22 is placed above the accommodation cylinder 58. The lower portion of the solid-liquid separator 20 is thickly extended so that a wide opening cannot be caused between the solid-liquid separator 20 and the inner surface of the accommodation cylinder 58. This structure does not especially limit the length of the solid-liquid separator 20. For example, the solid-liquid separator 20 may be extended to the neighborhood of the liquid surface.

Effects and Advantages of the Invention

According to the present invention, in the reaction method by using the heterogeneous catalyst, when carrying out a separation of the heterogeneous catalyst and the reaction liquid, the separation of the heterogeneous catalyst and the reaction liquid can be carried out certainly and effectively by using the compact apparatus with inhibiting the side reaction or the polymerization and avoiding unstable operation due to clogs of the heterogeneous catalyst.

Particularly, the line screen for separating the heterogeneous catalyst particle and the reaction liquid has a sufficiently wider opening in the longitudinal direction than that in the lateral direction. Therefore, the reaction liquid is little hindered to pass even if the opening width is made narrow. In addition, the opening of the line screen is little clogged or attached even in the formation reaction of viscous or adhesive polymers.

DETAILED DESCRIPTION OF THE PREFERRED EMBODIMENTS

Hereinafter, the present invention is more specifically illustrated by the following examples of some preferred embodiments. However, the present invention is not limited thereto.

FIXED BED REACTION

EXAMPLE 1

The reaction to produce methyl acrylate is carried out by use of a fixed bed reaction apparatus.

Product: methyl acrylate

Raw materials: acrylic acid, methanol

Reactor: fixed bed reaction apparatus (refer to FIG. 1) having a diameter of 1,400 mm, a height of 2,300 mm, a body-portion capacity of 3.5 m$^3$, and charged resin of 2.0 m$^3$.

Solid-liquid separator: Johnson screen (commercial name, Nikki Universal) is cylindrical, and the effective portion for filtration (line screen) is placed up to 10 mm below the partition plate (refer to FIG. 2). Outer diameter of cylindrical screen: 50 mm, effective length: 170 mm, width of line material: 1.5 mm, opening width: 0.3 mm, number of placing: 20 pieces (13.0 pieces/m$^2$), effective filtration area: 0.534 m$^2$ (0.027 m$^2$/piece), and opening portion area: 0.089 m$^2$ (0.0044 m$^2$/piece).

Passing liquid amount: passing liquid amount: 1.67 m$^3$/h, liquid density: 900 kg/m$^3$, passing velocity for effective filtration area: 0.87 mm/s, passing linear velocity for the opening portion: 5.2 mm/s, and flow downward from the upper portion to the lower portion of reactor.

Heterogeneous catalyst: DIAION PK-208 (commercial name, Mitsubishi Chemical corp., porous cation-exchange resin containing p-toluenesulfonic acid as a major component, 15% particle diameter about 700 μm, and 15% particle diameter: about 500 μm).

Results as Carried Out

Composition at the inlet of the reactor: main raw material (acrylic acid) 50%, supplementary raw material (methanol) 20%, product (methyl acrylate) 15%, and water.

Composition at the outlet of the reactor: main raw material (acrylic acid) 30%, supplementary raw material (methanol) 5%, product (methyl acrylate) 40%, water 10%, and impurities 15%.

Conversion: 35 to 40%.

100 hours later: no problem in operation.

1000 hours later: no problem as to heterogeneous catalyst particle. Polymers were not attached at all. A slight amount of polymer was attached to the supporting structure of the line screen, but it could easily be removed.

EXAMPLE 2

A solid-liquid separator of which line screen portion was placed in a state of protruding 15 mm over the partition plate was used as Johnson screen of the solid-liquid separator in Example 1. The interval is made between the lower end of the line screen and the surface of the partition plate, and the solid-liquid separator has a structure of piling the reaction liquid a little on the partition plate.
Results as Carried Out When 1,000 hours passed from carrying out the reaction polymers were attached to the supporting structure of the line screen. Clogs were caused on a half of the line materials. However, they were removed by carrying out jet washing. Some line materials were washed with a brush.

EXAMPLE 3

The reaction to produce methyl methacrylate was carried out. The explanation of the condition common to Example 1 is omitted.

Product: methyl methacrylate

Raw materials: methacrylic acid, methanol

Reactor: fixed bed reaction apparatus (refer to FIG. 1) having a diameter of 1,800 mm, and a height of 2,500 mm, used in a state of full.

Solid-liquid separator: Johnson screen (commercial name, Nikki Universal), outer diameter of cylindrical screen: 60 mm, effective length: 170 mm, width of line material: 1.5 mm, opening width: 0.15 mm, number of placing: 20 pieces (4.8 pieces/m$^2$), effective filtration area: 0.64 m$^2$ (0.032 m$^2$/piece), and opening portion area: 0.058 m$^2$ (0.0029 m$^2$/piece).

Passing liquid amount: passing liquid amount 3.00 m$^3$/h, liquid density: 900 kg/m$^3$, passing velocity for effective filtration area: 1.30 mm/s, passing linear velocity for the opening portion: 14 mm/s.

Heterogeneous catalyst the same as of Example 1
Results as Carried Out

Reaction temperature: 70° C.

Composition at the inlet of the reactor: main raw material (methacrylic acid) 61%, supplementary raw material (methanol) 9%, and product (methyl methacrylate) 27%.

Composition at the outlet of the reactor: rain raw material (methacrylic acid) 45%, supplementary raw material (methanol) 3%, and product (methyl methacrylate) 46%.

The reaction temperature is operated so as to adjust the conversion to 25%.

4 months later: The reaction temperature was 79° C. It could be confirmed that the life of the heterogeneous catalyst particle is more effectively extended than that of Example 4. There were no problems as to the heterogeneous catalyst particle when the continuous operation was carried out for 4 months. Polymers were not attached at all. A slight amount of polymer was attached to the supporting structure of the line screen, but it could easily be removed.

EXAMPLE 4

The solid-liquid separator was changed to the structure of Example 2 in Example 3. Concretely, a solid-liquid separator of which line screen portion was placed in a state of protruding 15 mm over the partition plate was used as Johnson screen of the solid-liquid separator.
Results as Carried Out Reaction temperature: 70° C.

Composition at the inlet of the reactor: main raw material (acrylic acid) 61%, supplementary raw material (methanol) 9%, and product (methyl acrylate) 27%.

Composition at the outlet of the reactor: main raw material (acrylic acid) 45%, supplely raw material (methanol) 3%, and product (methyl acrylate) 45%.

4 months later: The reaction temperature was 83° C. There were no problems as to the heterogeneous catalyst particle when the continuous operation was carried out for 4 months. Polymers were attached to the supporting structure of the line screen. Clogs were caused on a half of the line materials. However, they were removed by out jet washing. Some line materials were washed with a brush.

EXAMPLE 5

The packing condition of the heterogeneous catalyst particle was changed in Example 3. The explanation of the condition common to Example 3 is omitted.

Concretely, the heterogeneous catalyst particle was classified, and divided into a large particle portion having a particle diameter of 700 to 1,200 $\mu$m (5% of the whole), and a small particle portion having a particle diameter of 300 to 700 $\mu$m (95% of the whole). As is shown in FIG. 1, after being packed with the large particle portion up to a position slightly higher than the solid-liquid separator at the bottom side of the reactor 10, then the reactor was packed with the small particle portion thereon.
Results as Carried Out Reaction temperature: 77° C.

4 months later: The reaction temperature was 77° C. There were no problems as to the heterogeneous catalyst particle when the continuous operation was carried out for 4 months. Polymers were not attached at all. A very slight amount of polymer as attached could easily be removed.

COMPARATIVE EXAMPLE 1

The same condition as of Example 2 was employed except that a wire mesh strainer was used as a solid-liquid separator.

Solid-liquid separator: wire mesh stainer, cylindrical, 50 mesh. The effective portion for filtration is placed 15 mm over the partition plate.
Results as Carried Out 100 hours later: The reactivity and selectivity became lower, and the pressure loss tended to rise.

When about 500 hour passed, the operation was difficult to continue. Therefore, the inspection was carried out. Then, the mesh of the strainer was clogged with fine materials of the heterogeneous catalyst particle. A great deal of viscous materials and polymers were attached. It was in necessary to exchange the mesh. The polymers were attached to the supporting structure of the strainer.

FLUIDIZED BED REACTION

EXAMPLE 6

The reaction to produce 2-ethylhexyl acrylate was carried out by use of a fluidized bed reaction apparatus.

Product: 2-ethylhexyl acrylate

Raw materials: acrylic acid, 2-ethylhexanol

Reactor: stainless-made fluidized bed reaction apparatus (refer to FIG. 5) with a dehydration packed column (100$\phi$), having a diameter of 500 mm, a capacity of 100 l, and charged amount (reaction liquid+heterogeneous catalyst particle: 70 liter, and heterogeneous catalyst particle: 18 liter (in a dry state)), heating jacket/charging steam.

Solid-liquid separator: Johnson screen (commercial name, Nikki Universal) is cylindrical, and attached at outer bottom circumference of the reactor. Outer diameter of cylindrical screen: 34 mm, effective length: 60 mm, width of element (line material): 1.5 mm, opening width: 0.15 mm, number of placing: 1 piece (3.1 piece/m²), effective filtration area: 0.0064 m², and opening portion area: 0.00058 m². The solid-liquid separator of which structure is shown in FIG. 6(c) was placed upward with rotation of 90°.

Passing liquid amount: passing liquid amount: 0.039 m³/h, liquid density: 900 kg/m³, passing velocity for effective filtration area: 3.17 mm/s, passing linear velocity for the opening portion: 18 mm/s, and flow downward from the upper portion to the lower portion of reactor.

Stirrer: Pfaudler blade, ratio of blade diameter: 0.7, and blade tip velocity: 4 m/s.

Heterogeneous catalyst: the same as of Example 1
Results as Carried Out

Reactor pressure: 70 mmHg
Composition at the inlet of the reactor: main raw material (acrylic acid) 49%, supplementary raw material (2-ethylhexanol) 35.6%, product (2-ethylhexyl acrylate) 14.2% and water 0.1%. The alcohol was supplied from the reactor (23.5 kg/h) and the column top (13.2 kg/h), and phenothiazine of 0.05% of the main raw material was added from the column top.

Composition at the outlet of the reactor: main raw material (acrylic acid) 13.2%, supplementary raw material (2-ethylhexanol) 25.7%, product (2-ethylhexyl acrylate) 59.6%, water 0.4%, and reaction liquid 34.8 kg/h. 1.7 kg/h of water phase and 0.18 kg/h of oil phase were extracted.

Conversion: 60% (acrylic acid), and 58% (alcohol).
Selectivity: 98.4% (acrylic acid), and 98.5% (alcohol).
Impurities: 0.26% (dimer acid 2-ethylhexyl etc.)
When 150 hour passed, the inspection was carried out. Polymers were not observed.

1,000 hours later: The opening of the screen was clogged with resins. Polymers were not attached. No problem.

EXAMPLE 7

The reaction to produce hydroxylpropyl acrylate is carried out.

Product: hydroxylpropyl acrylate
Raw materials: acrylic acid, propylene oxide
Reactor: the same as of Example 6 except for charging with 48 liter of the heterogeneous catalyst particle (in a moist state), and cooling by steaming cold water into the jacket.

Solid-liquid separator: Johnson screen (commercial name, Nikki Universal) is cylindrical, and attached at a fluidized portion of the reaction liquid at outer bottom circumference of the reactor (refer to FIG. 6(b)). Outer diameter of cylindrical screen: 34 mm, effective length: 30 mm, width of element (line material): 1.5 mm, opening width: 0.15 mm, number of placing: 1 piece (3.1 pieces/m²), effective filtration area: 0.0032 m², and opening portion area: 0.00029 m².

Passing liquid amount: passing liquid amount: 0.031 m³/h, liquid density: 900 kg/m³, passing velocity for effective filtration area: 2.7 mm/s, and passing linear velocity for the opening portion: 30 mm/s.

Stirrer: the same as of Example 6
Heterogeneous catalyst DIMON PK-316 (commercial name, Mitsubishi Chemical corp., amine-based anion-exchange resin, 15% particle diameter, about 700 μm, and 15% particle diameter: about 450 μm).
Results as Carried Out
Reaction temperature: 80° C.
Composition at the inlet of the reactor: main raw material (acrylic acid) 45 weight %, and supplementary raw material (propylene oxide) 55 weight %.

Piling time: The raw materials were added to adjust the piling time to 1 hour.
Conversion: 80%.
100 hours later: No problem.
1,000 hours later: Polymers were not attached.

EXAMPLE 8

The separation of solid and liquid was carried out by use of 2-hydroxyethyl acrylate.

Reactor: the same as of Example 7 except that the reactor was stainless-made and had a capacity of 20 liter, and that the reactor was charged with the heterogeneous catalyst of 60% of the reactor.

Solid-liquid separator: the same as of Example 7
Passing liquid amount: passing liquid amount 0.0095 m³/h, and liquid density: 1,050 kg/m³.

Stirrer: paddles (3 piece), ratio of blade diameter: 0.4, and blade tip speed: 1.5 m/s.

Heterogeneous catalyst: the same as of Example 7
Results as Carried Out
Operation temperature: 60° C.
100 hours later: No problem.
1,000 hours later: No problem. Stable operation. No clogs.

COMPARATIVE EXAMPLE 2

The same condition was employed except for using a wire mesh of 80 mesh as the solid-liquid separator in Example 6.

Solid-liquid separator: The wire mesh of 80 mesh (diameter 100 mm) was attached to the extracting tube of the reactor bottom. Width of mesh line material: 1.5 mm, opening width: 0.17 mm, opening ratio: 25%, effective filtration area: 0.0079 m², and opening portion area: 0.0019 m².

Passing liquid amount: passing liquid amount: 0.039 m³/h, liquid density: 900 kg/m³, passing velocity for effective filtration area: 1.4 mm/s, and passing linear velocity for the opening portion: 5.5 mm/s, (and flow downward from the upper portion to the lower portion of reactor).

Stirrer and heterogeneous catalyst: the same as of Example 6
Results as Carried Out
When 150 hours passed, it was clogged with resins and the pressure loss tended to rise. Therefore, the operation was stopped and the inspection was carried out.

The mesh was clogged with the heterogeneous catalyst. In addition a great deal of clogs due to attaching polymers were observed. The solid-liquid separator was in to recover after washing it enough.

COMPARATIVE EXAMPLE 3

The same condition as of Example 6 was employed in the same way as of Comparative Example 2 except for using a wire mesh of 80 mesh as the solid-liquid separator.

Solid-liquid separator The wire mesh of 80 mesh (diameter 100 mm) was attached at outer circumference of the reactor bottom. The attached position thereof is outside of 50% or more of the blade diameter of the stirrer. Outer diameter of cylindrical mesh: 34 mm, effective length: 60 mm, width of mesh line material: 0.15 mm, opening width: 0.17 mm, number of placing: 1 piece (3.14 pieces/m²), effective filtration area: 0.0064 m², and opening portion area: 0.00016 m².

Passing liquid amount: passing liquid amount: 0.039 m³/h, liquid density: 900 kg/m³, passing velocity for effective filtration area: 1.7 mm/s, passing linear velocity for the opening portion: 7 mm/s, and flow downward from the upper portion to the lower portion of reactor.

Stirrer and heterogeneous catalyst: the same as of Example 6

Results as Carried Out 500 hours later: The mesh was clogged with resins a little. The mesh was washed because of attaching a small amount of polymers.

COMPARATIVE EXAMPLE 4

The formation reaction as of Example 7 was carried out in combination of the reactor and the sedimentation tank.

A solid-liquid separator was not placed at the reactor, and the slurry liquid comprising the reaction liquid and the heterogeneous catalyst particle extracted from the reactor was sent out a weight-sedimentation tank (40 mmφ×100 mm height), and then the supernatant was extracted. The sedimentation tank was also cooled with a cooling jacket (1 liter/hr circulation).

Results as Carried Out

When three hours passed, the tendency of raising temperature in the sedimentation tank was observed. The trouble of the circulation pump was observed, and then stopped. Polymers and solidified heterogeneous catalyst were observed.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A reaction method using a heterogeneous catalyst for reacting a reaction liquid, said method comprising the steps of: (a) supplying a reaction liquid into a reactor containing a heterogeneous catalyst particle and reacting said reaction liquid in the presence of the heterogeneous catalyst particle to produce a reaction product, and (b) passing the resultant reaction liquid product containing the heterogeneous catalyst particle through a line screen having a substantially uniform opening width that is narrower than the 15% particle diameter where said opening width allows less than 15% of said heterogeneous catalyst particles to pass substantially through said opening, and where said opening has maximal dimension and a minimal dimension and has a ratio of said maximal and minimal dimension of 1.0 to 1.5, separating said liquid reaction product from said catalyst, and then extracting the reaction liquid product separated from the heterogeneous catalyst particle from the reactor.

2. A reaction method using a heterogeneous catalyst according to claim 1, wherein: the line screen is a cylindrical screen which is obtained by helically coiling a line material at intervals; the line material of the cylindrical screen has a tapered cross section which is thick outside of the cylindrical screen and narrow inside thereof; said method comprising passing the reaction liquid product from an outside of the cylindrical screen to an inside thereof in the step of (b).

3. A reaction method using a heterogeneous catalyst according to claim 1, which further comprises the step of (−a) packing the reactor with the heterogeneous catalyst particle before carrying out the step of (a), said packing step comprising placing the heterogeneous catalyst particle having a comparatively larger particle diameter at the position adjacent to the line screen and placing the heterogeneous catalyst particle having a comparatively smaller particle diameter at the position apart from the line screen in the step of (−a).

4. A reaction method using a heterogeneous catalyst according to claim 2, which further comprises the step of (−a) packing the reactor with the heterogeneous catalyst particle before carrying out the step of (a), passing the reaction liquid from an upper portion to a lower portion of the reactor packed with the heterogeneous catalyst particle in the step of (a); and placing the cylindrical screen over a partition plate located at a bottom of the space packed with the heterogeneous catalyst particle in the reactor so that the interval between the opening where the reaction liquid passes and an upper surface of the partition plate is not larger than 5 mm in the step of (b).

5. A reaction method using a heterogeneous catalyst according to claim 1, comprising reacting in step (a) said reaction liquid while fluidizing said reaction liquid and said heterogeneous catalyst particle to suspend and disperse said heterogeneous catalyst particle in said reaction liquid.

6. A reaction method using a heterogeneous catalyst according to claim 1, wherein the heterogeneous catalyst particle is an ion-exchange resin having an average particle diameter of 0.1 to 3 mm in the step of (a).

7. A reaction method using a heterogeneous catalyst according to claim 1, wherein said reaction liquid comprises alkylene oxide and (meth)acrylic acid and where said reaction method comprising producing hydroxyalkyl (meth)acrylate.

8. A reaction method using a heterogeneous catalyst according to claim 1, wherein said reaction liquid comprises (meth)acrylic acid and said reaction method comprising producing (meth)acrylate.

9. The reaction method using a heterogeneous catalyst according to claim 1, wherein the ratio of maximal and minimal values of the mesh opening scatter of said line screen is determined in the range of 1.0 to 1.2 times.

10. The reaction method using a heterogeneous catalyst according to claim 1, wherein said opening width of the respective line material is in the range of 0.05 mm to 2 mm.

* * * * *